United States Patent [19]

Meis et al.

[11] 4,402,860
[45] Sep. 6, 1983

[54] PROCESS FOR DEMETALLIZING PRIMARY PRODUCTS OF THE OXO SYNTHESIS

[75] Inventors: Josef Meis; Volkmar Schmidt; Hans Tummes; Joachim Much, all of Oberhausen, Fed. Rep. of Germany

[73] Assignee: Ruhrchemie Aktiengesellschaft, Oberhausen, Fed. Rep. of Germany

[21] Appl. No.: 296,042

[22] Filed: Aug. 25, 1981

[30] Foreign Application Priority Data

Aug. 27, 1980 [DE] Fed. Rep. of Germany ....... 3032252

[51] Int. Cl.$^3$ ...................... B01J 31/40; C22B 23/00; C07C 45/50; C07C 27/22
[52] U.S. Cl. ..................................... 252/420; 75/119; 423/141; 568/456; 568/909; 422/198
[58] Field of Search ........................... 252/420, 411 R; 423/141; 75/108, 119, 0.5 AA; 568/456, 451

[56] References Cited

U.S. PATENT DOCUMENTS

| | | | |
|---|---|---|---|
| 2,581,988 | 1/1952 | Spijker et al. ...................... | 568/451 |
| 2,593,232 | 4/1952 | Watson ........................... | 252/411 R |
| 2,779,796 | 1/1957 | Munger ............................. | 568/456 |
| 2,779,802 | 1/1957 | Harlan, Jr. ..................... | 75/0.5 AA |

FOREIGN PATENT DOCUMENTS 520802 1/1956 Canada ............................. 568/456

Primary Examiner—P. E. Konopka
Attorney, Agent, or Firm—Sprung, Horn, Kramer & Woods

[57] ABSTRACT

An improved process for de-cobaltizing the primary product of an oxo synthesis is disclosed wherein the primary product is contacted with steam introduced into a vessel to which the primary oxo product is introduced but initially maintained in out of contact relationship to such product by a cooling medium whereby heat transfer from the steam to the primary product is initially avoided. The primary product and steam are fed to a cylindrical reactor having a conical base, and after the steam has risen $\frac{1}{2}$ to $\frac{2}{3}$ of the height of the conical base it comes in contact with the primary product whose liquid level height in the vessel is maintained at one to two times the vessel's diameter. An apparatus for performing such process is also disclosed.

2 Claims, 2 Drawing Figures

PROCESS FOR DEMETALLIZING PRIMARY PRODUCTS OF THE OXO SYNTHESIS

BACKGROUND OF THE INVENTION

1. Field of the Invention

The present invention relates to a process for demetallizing primary products of the oxo synthesis with steam.

2. Discussion of Prior Art

In the known technical oxo processes, olefins are converted with carbon monoxide and hydrogen at elevated temperature and pressure in the presence of cobalt compounds. The products thereby formed ("primary products"), consisting mainly of primary aldehydes and alcohols, contain the cobalt used as catalyst dissolved in the form of cobalt carbonyl compounds. These cobalt carbonyls complicate the further processing of the primary products, e.g. their distillation and hydrogenation, to such an extent that, for economic reasons, they have to be removed in a separate operating stage ("de-cobaltization").

The economy of technical oxo processes depends decisively on carrying out the cobalt carbonyl decomposition in such a manner that the resulting cobalt or cobalt compounds can easily be separated from the organic reaction products and recycled to the hydroformylation stage without great effort and expense.

Of the many known processes for de-cobaltizing the primary oxo products, the use of steam is particularly characterized by its economy and the advantage that the higher condensation products contained in the crude oxo products are at the same time partially cracked. Depending on the reaction conditions employed, above all on the sulphur levels in the reaction system, various decomposition products are obtained from the cobalt carbonyl compounds in the steam treatment, namely cobalt metal or preferentially cobalt hydroxide or, especially in the presence of acids, cobalt salts of these acids.

It is known from French Pat. No. 1,018,055 to decompose the cobalt carbonyl compounds contained in the primary product of the oxy synthesis with steam, with the formation of finely divided cobalt metal. After cooling the mixture and removing the gases from the head of the reactor, the metal can be separated by mechanical separation devices from the organic phase containing the products of the oxo synthesis.

In carrying out this process it has been found that in most cases only part of the cobalt is precipitated as metal, the rest being found in dissolved form in the aqueous phase. Additionally, this known procedure does not insure that the cobalt metal is always obtained in an easily separable, e.g. filterable, state.

According to the teaching of U.S. Pat. No. 2,779,796 the soluble cobalt compounds can, by treating the crude product with steam, be separated to such an extent by decomposition or precipitation that no extensive contamination of the connected apparatus occurs if, during the treatment of the crude product with steam, all contact with a fixed heating surface whose temperature is higher than the boiling point of the water-product mixture is avoided. In this process the crude product, instead of being treated in a stirred boiler, can alternatively also be treated by mixing together the streams of steam and oxygen-containing crude product in a turbulent flow field, such as exists for example in a mixer tube. This process can, however, only be used in the case of crude oxo products having very low Co contents of 0.1% and less. Such small Co concentrations in the oxo synthesis require over-large reaction volumes and high hydroformylation temperatures, and are thus economically unsuitable for, in particular, low molecular weight olefins. Moreover, despite the low Co concentration only about 90% Co is removed. With the Co concentrations conventionally used in this technology, Co would be deposited in a metallically stable and permanent manner on the stirrers and mixer tubes with this process.

The similar mixing of crude oxo product with hot water in a tube is described in German Pat. No. 10 24 499. With this process, too, the degree of de-cobaltization is, however, unsatisfactory and results in serious obstructions throughout the entire system as well as in the post-treatment apparatus.

It is an object of this invention, therefore, to provide a process which avoids the aforementioned disadvantages and guarantees a complete separation of the cobalt in such a form as to permit its direct reuse in the hydroformylation.

SUMMARY OF THE INVENTION

According to the invention, the decomposition of the cobalt carbonyl compounds dissolved in the primary reaction product of the oxo synthesis into solid cobalt-containing products, largely cobalt metal, is carried out by intimate mixing at 100° to 200° C. and 5 to 25 bars in a cylindrical vessel without built-in fitments and immediate reuse of the cobalt products seperated from the reaction products in the oxo synthesis, and is characterized in that the cylindrical reaction vessel has a conical base, the steam is led continuously from below through a cooled nozzle located at $\frac{1}{2}$ to $\frac{2}{3}$ the height of the conical base, thence flows upwardly at a rate of 50 to 150, preferably 80 to 120 m/second coaxially to the cylindrical reaction vessel and thereby comes into contact, immediately after exiting, with the cobalt carbonyl-containing oxo product introduced into a steam flow cone provided therefor, the liquid level being maintained at a height corresponding to 1 to 2 times the diameter of the cylindrical reaction vessel by continuously removing the reaction product at the lowest point of the conical base in the cylindrical reaction vessel.

The complete decomposition of the metal carbonyl compounds is not only a requirement for a trouble-free working up of the demetallized oxo product, but is also a prerequisite that no Co metal is deposited in the demetallizing system.

Accordingly, the complete decomposition of the cobalt carbonyls, which may be contaminated by small amounts of other metal carbonyls, e.g. of iron, is carried out according to the invention under conditions which insure that in the thorough mixing of the primary product and steam, cobalt particles are obtained in such a form and size that they remain in motion and are not deposited. It is important that the decomposition spaced has as small a surface area as possible and has no type of built-in fitments, with the exception of equipment for adding primary product and steam.

A sufficiently good movement of the primary product to prevent deposition of the cobalt produced by the decomposition is achieved by partially depressurizing the residual synthesis gas still dissolved in the primary product and by blowing in steam at a speed of 50 to 150 m/second, at best 80 to 120 m/second, centrally at the base of the decomposition vessel and a short distance above the base outlet.

The primary product is added diametrically to the steam addition from above, in which case the inlet pipe dips only slightly into the liquid phase, or is added from below immediately adjacent the steam inlet.

In order to maintain the cobalt formed by decomposition fully in motion and in order to avoid the additional formation of higher boiling point byproducts, the residence time of the primary product in the decomposition space is adjusted to 4 to 15 minutes, and, in the case of aldehydes with 3 to 5 carbon atoms, preferably to 6 to 10 minutes.

It is necessary to raise the temperature in the decomposition space with increasing cobalt levels as well as with increasing C number of the primary product. The change in the cobalt level in the range that is of interest in the present process produces only a relatively slight shift in the decomposition temperature. An increase in the cobalt level in the primary product from 0.6% by weight to 1.0% by weight results in a rise in the temperature in the decomposition space of only 2° to 3° C. The decomposition temperature is influenced to a somewhat greater extent by the C number of the primary product. Thus, for example, in the same demetallizing apparatus and at a constant cobalt concentration of the primary product of approximately 0.6% by weight, for a primary product of propylene temperatures in the decomposition space of between 145° C. and 155° C. are necessary, and for a primary product of tetrapropylene temperatures of 155° C. to 160° C. are necessary.

In order to achieve an optimum de-cobaltization, the pressure in the decomposition space is adjusted to the required decomposition temperature according to the process of the invention in such a way that about 15 to 45% of the primary product occurs, together with the waste gas dissolved in the primary product, in vapor form at the head of the decomposition vessel.

Most of the demetallized primary product, which entrains some steam condensate with small amounts of cobalt dissolved therein, is removed at the base of the decomposition vessel. The base is preferably formed as a cone in order to avoid cobalt deposits.

In the previously known de-cobaltization processes not involving acid, there is the danger that the waste gas/vapor line may become blocked by entrained cobalt dust. Such blockages are avoided in the process according to the invention if the gas space above the liquid space forming the decomposition zone is at least as large as the latter. Preferably, the gas space is 1½ times as large as the liquid space. If the process is carried out with an insufficiently large gas space, the waste/gas vapor line must be cooled as much as possible before it reaches the cooler inlet.

BRIEF DESCRIPTION OF DRAWINGS

Referring to the drawings.

DESCRIPTION OF SPECIFIC EMBODIMENT

Figure 1:
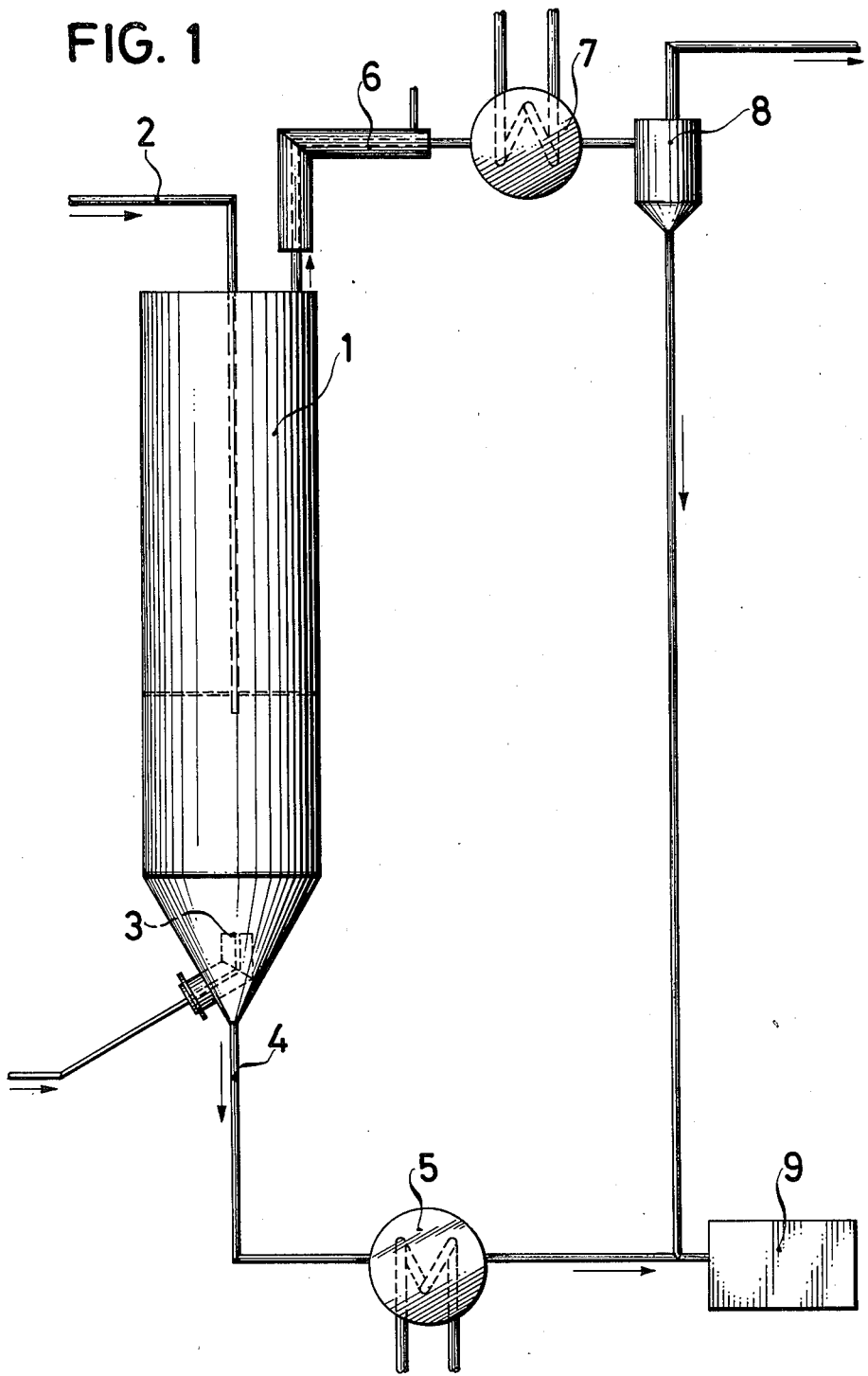
FIG. 1 is a schematic drawing showing an apparatus for carrying out the invention.

In carrying out the process according to the invention, it has proved advantageous, especially in the case of decomposition vessels of large diameters, to introduce the primary product and steam into the reaction vessel by means of a device illustrated in FIG. 2 and described in more detail hereinafter. This device involves a combined nozzle for primary product and steam, which which is cooled with water. The device consists of a core tube 11 through which the reaction product is introduced, and an annular space 12 around the core tube or consisting of tubes arranged annularly around the core tube, through which the steam is introduced. In order to avoid heat transfer from the steam to the primary product, the core tube 11 is separated from the annular space 12 or the annularly arranged tubes by a space 13 charged with a cooling medium.

EXAMPLE 1

Primary product which contains 3 to 6 g Co/l in the form of dissolved carbonyl compounds and which comes directly from a high pressure separator of the hydroformylation centrally from above via a line 2 which dips into a liquid column, is depressurized in a cylindrical vessel (reaction vessel 1) equipped with a conical base.

Steam at a pressure of 20 to 40 bars is blown in at a speed of about 100 m/second a short distance above the cone outlet through a nozzle 3 whose outlet is directed vertically in alignment with the primary product inlet. The decomposition temperature is between 150° and 160° C., and a pressure of 17 to 19 bars is maintained.

All of the cobalt, 70% of the steam used, in the form of a heterogeneous aqueous phase containing some cobalt, and about 70% of the demetallized primary product, are withdrawn from the cone outlet 4 via a cooler 5. Uncondensed steam, about 30% of the demetallized primary product, as well as the residual gas which was dissolved in the primary product of the oxo synthesis leave the top of the decomposition vessel via line 6.

After passing through a cooling stage 7 and a gas separation stage 8, the liquid products are recombined and passed to a phase separation stage 9. After decomposition of the carbonyls and separation of the solid cobalt, the primary product contains less than 0.1% of the original Co concentration. The separated cobalt sediment is reused directly in the hydroformylation. The aqueous solution, which contains small amounts of cobalt, can be treated e.g. with alkali hydroxides to precipitate cobalt, which is reused in the hydroformylation.

EXAMPLE 2

A cylindrical vessel having a conical base serves as decomposition vessel.

Primary product coming directly from the oxo synthesis and produced from diisobutylene is introduced into the decomposition vessel, in the same way as described in Example 1. Steam (25 to 30 bars) is fed in at the same time through a nozzle. The decomposition of the carbonyls is carried out at 160° to 170° C. and at about 16 bars. The de-cobaltized, waterclear product contains about 5 mg Co/l.

EXAMPLE 3

Figure 2:
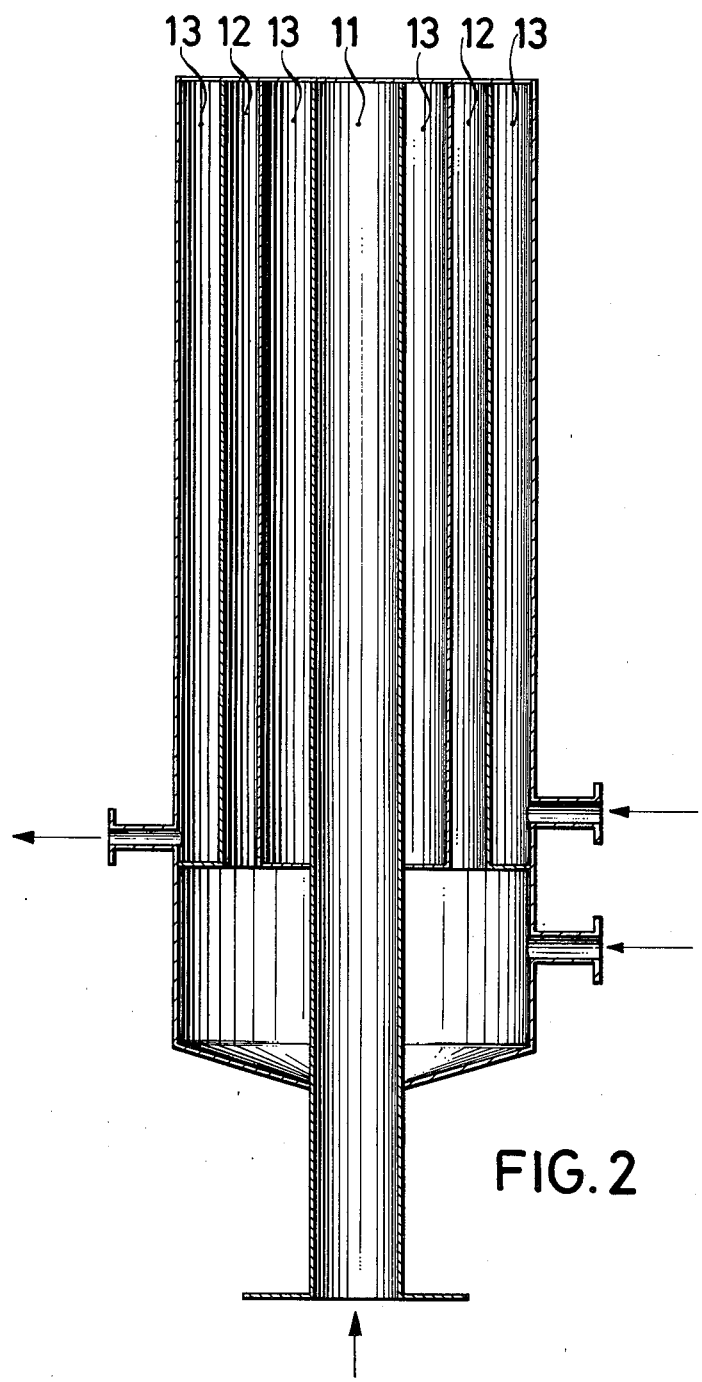
FIG. 2 is an enlarged vertical section of a primary product/steam feed device preferably employed in the apparatus of FIG. 1.

A combined, water-cooled feed device is located in the conical base of a cylindrical vessel, as illustrated in FIG. 2.

Primary product from the hydroformylation of propylene is introduced through a core tube 11, while steam at 28 bars is forced in through a plurality of steam nozzles 12. The feed device combination is surrounded by a cooling jacket 13. Decomposition takes place at a temperature of 150° to 160° C. and at a pressure of about 19 bars. After the de-cobaltization the primary product contains 3 mg Co/l.

What is claimed is:

1. In a process for decomposing the cobalt carbonyl compounds dissolved in the primary reaction product of the oxo synthesis into solid cobalt-containing products, largely into cobalt metal, by intimately mixing the primary reaction product with steam at 100° to 200° C. and at 5 to 25 bars in a cylindrical vessel without built-in fitments and directly reusing the cobalt products separated from the reaction products for the oxo synthesis, the improvement wherein the cylindrical reaction vessel has a conical base, the steam is led continuously from below through a cooled nozzle located at $\frac{1}{2}$ to $\frac{2}{3}$ the height of the conical base whereby the steam forms a flowing cone, thence flows upwardly at a rate of 50 to 150 m/second, coaxially to the cylindrical reaction vessel and thereby comes into contact, immediately after exiting, with the cobalt carbonyl-containing oxo product introduced into said flowing cone, the liquid level is maintained at a height corresponding to 1 to 2 times the diameter of the cylindrical reaction vessel by continuously removing the reaction product at the lowest point of the conical base in the cylindrical reaction vessel.

2. A process according to claim 1 wherein the steam is caused to flow upwardly at a rate of 80 to 120 m/second.

* * * * *